(12) United States Patent
Laakkonen (10) Patent No.: US 7,606,606 B2
(45) Date of Patent: Oct. 20, 2009

(54) PATIENT MONITORING DEVICE WITH MULTIPLE SENSORS

(75) Inventor: Marko Laakkonen, Vantaa (FI)

(73) Assignee: General Electric Company, Schenectady, NY (US)

( * ) Notice: Subject to any disclaimer, the term of this patent is extended or adjusted under 35 U.S.C. 154(b) by 341 days.

(21) Appl. No.: 11/646,042

(22) Filed: Dec. 27, 2006

(65) Prior Publication Data
US 2007/0149865 A1    Jun. 28, 2007

Related U.S. Application Data

(63) Continuation-in-part of application No. 11/319,014, filed on Dec. 27, 2005, now abandoned.

(51) Int. Cl.
*A61B 5/1455* (2006.01)
(52) U.S. Cl. ........................ 600/310; 600/336
(58) Field of Classification Search .......... 600/309–344
See application file for complete search history.

(56) References Cited

U.S. PATENT DOCUMENTS

| | | | |
|---|---|---|---|
| 4,860,759 A * | 8/1989 | Kahn et al. ................ 600/481 |
| 5,025,791 A | 6/1991 | Niwa | |
| 5,218,962 A | 6/1993 | Mannheimer et al. | |
| 5,818,985 A * | 10/1998 | Merchant et al. .............. 385/20 |
| 6,134,460 A * | 10/2000 | Chance ........................ 600/342 |
| 6,537,225 B1 * | 3/2003 | Mills ........................... 600/323 |
| 6,597,933 B2 | 7/2003 | Kiani et al. | |
| 6,615,065 B1 * | 9/2003 | Barrett et al. ............... 600/340 |
| 6,714,804 B2 | 3/2004 | Al-Ali et al. | |
| 6,760,610 B2 | 7/2004 | Tschupp et al. | |
| 6,879,850 B2 * | 4/2005 | Kimball ...................... 600/336 |
| 7,193,957 B2 * | 3/2007 | Masui et al. ................. 369/121 |
| 7,403,805 B2 * | 7/2008 | Abreu ......................... 600/318 |

FOREIGN PATENT DOCUMENTS

GB        2 392 242    2/2004

\* cited by examiner

*Primary Examiner*—Eric F Winakur
(74) *Attorney, Agent, or Firm*—Andrus, Sceales, Starke & Sawall, LLP (57) ABSTRACT

The invention relates to a patient measurement device, especially to a pulse oximeter, provided with multiple sensors. In order to reduce the hardware required by a measurement performed through the multiple sensors, a repeating drive pulse sequence is generated, which contains drive pulses for the emitter elements of the plurality of sensors. Furthermore, each drive pulse of the sequence is supplied to a corresponding emitter element and sensor-specific detectors connected in parallel are employed to produce an electric reception signal received at the measurement device.

22 Claims, 6 Drawing Sheets

PATIENT MONITORING DEVICE WITH MULTIPLE SENSORS

CROSS REFERENCE TO RELATED APPLICATION

The present application is a continuation-in-part of U.S. patent application Ser. No. 11/319,014, filed on Dec. 27, 2005 now abandoned.

FIELD OF THE INVENTION

The present invention relates generally to patient monitoring. More particularly, the present invention relates to monitoring devices and systems provided with a plurality of sensors and configured to determine the attenuation of light in a subject. The monitoring device is typically a pulse oximeter.

BACKGROUND OF THE INVENTION

Pulse oximetry is at present the standard of care for continuous monitoring of arterial oxygen saturation ($SpO_2$). Pulse oximeters provide instantaneous in-vivo measurements of arterial oxygenation, and thereby an early warning of arterial hypoxemia, for example.

A pulse oximeter comprises a computerized measuring unit and a sensor attached to the patient, typically to a finger or ear lobe. The sensor includes a light source for sending an optical signal through the tissue and a photo detector for receiving the signal after transmission through the tissue. On the basis of the transmitted and received signals, light absorption by the tissue can be determined. During each cardiac cycle, light absorption by the tissue varies cyclically. During the diastolic phase, absorption is caused by venous blood, tissue, bone, and pigments, whereas during the systolic phase there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood.

Light transmission through an ideal absorbing sample is determined by the known Lambert-Beer equation as follows:

$$I_{out}=I_{in}e^{-\epsilon DC} \qquad (1)$$

where $I_{in}$ is the light intensity entering the sample, $I_{out}$ is the light intensity received from the sample, D is the path length through the sample, $\epsilon$ is the extinction coefficient of the analyte in the sample at a specific wavelength, and C is the concentration of the analyte. When $I_{in}$, D, and $\epsilon$ are known, and $I_{out}$ is measured, the concentration C can be calculated.

In pulse oximetry, in order to distinguish between two species of hemoglobin, oxyhemoglobin ($HbO_2$), and deoxyhemoglobin (RHb), absorption must be measured at two different wavelengths, i.e. the sensor normally includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

Conventional pulse oximeters are restricted to measurement of arterial oxygen saturation at a single tissue site. Therefore, if continuous and simultaneous oxygen status measurements are needed from several tissue sites, a straightforward method is to use a plurality of conventional pulse oximeters simultaneously. The need may arise, for example, during a delivery when both the mother and the infant need to be monitored simultaneously.

To eliminate the above drawback, pulse oximeters have been developed, which provide simultaneous and continuous measurement results from a plurality of tissue sites. U.S. Pat. No. 6,714,804 discloses a stereo pulse oximeter providing simultaneous and continuous oxygen status measurements at multiple tissue sites. The pulse oximeter is provided with multiple sensors attachable to distinct tissue sites. Each sensor may be connected through a separate cable and sensor interface to a signal processor. Alternatively, a so-called stereo sensor, which is provided with multiple branches, may connect the sensors through a common patient cable to a single connection at the pulse oximeter. From the said single connection each sensor signal is branched off to the respective sensor interface.

U.S. Pat. No. 5,218,962 further discloses a multiple region pulse oximetry probe and oximeter, which enable the blood characteristics to be sensed at two or more unique sites. In one embodiment, the probe housing accommodates probe elements for two distinct tissue regions, but the probe elements may also be mounted in separate probe housings. The oxygen saturation values obtained from two tissue sites are compared with each other to improve the reliability of the measurement.

A major problem in pulse oximetry concerns mechanical or motion artefacts, i.e. unwanted motion of the patient, which causes extra noise in the signal and may thus result in inaccurate $SpO_2$ readings and false alarms. To fight the motion artefact, pulse oximeters may be provided with motion sensors which detect patient movements. U.S. Pat. No. 5,025,791, for example, discloses a pulse oximeter with a physical motion sensor. If the motion sensor detects motion that continuously lasts longer than for a predetermined time, the photoelectric measurement signals are not utilized or the obtained readings are provided with an indication of the simultaneous physical motion.

A drawback related to current pulse oximeters providing simultaneous measurement results from a plurality of sensors is the rather extensive multiplication of the hardware required by the parallel measurements. As mentioned above, each sensor normally requires a dedicated interface that typically includes both signal processing means for the electric signal received from the respective sensor and current drivers for the emitters of the respective sensor. In a pulse oximeter provided with a motion sensor the integration of the motion sensor into the same device tends to convert the pulse oximeter to a dedicated device for which standard pulse oximeter components cannot anymore be utilized. The integration thus considerably increases the complexity of the device.

The present invention seeks to eliminate the above drawbacks and to bring about a novel mechanism for non-invasively obtaining measurement signals from a patient through a plurality of optical sensors.

SUMMARY OF THE INVENTION

The present invention seeks to provide a cost-effective measurement arrangement for monitoring a patient through a device provided with a plurality of optical sensors. The invention further seeks to improve the cost-effectiveness of a pulse oximeter provided with a plurality of sensors.

In the present invention, a monitoring device is operably connected to at least two sensors for measuring the attenuation of light simultaneously through the said sensors. Each sensor comprises at least one emitter element for emitting radiation and a sensor-specific detector for receiving the radiation and for producing an electric signal in response to the radiation. The sensor-specific detectors are connected in parallel to produce an electric reception signal at a terminal pair common to the sensor-specific detectors. As the drive pulses that activate a particular emitter element are supplied to that emitter element in pre-allocated time slots, the monitoring device knows when a particular detector generates the electric reception signal or which one of the detectors generates the electric reception signal in a particular time window. The electric reception signal may thus be supplied to the monitoring device through a single wire pair, which allows the use of a reception branch of a conventional single-sensor monitor, i.e. no hardware multiplication is necessary on the reception side of the monitoring device for receiving and processing signals from a plurality of sensors. Consequently, the sensors may be connected to the said reception branch through a single patient cable comprising a branch for each sensor and common cable segment comprising the above-mentioned single wire pair.

Thus one aspect of the invention is providing a measurement method for a measurement device configured to determine the attenuation of light in at least one subject. The method includes connecting the measurement device operably to a plurality of sensors, each sensor comprising at least one emitter element for emitting radiation and a sensor-specific detector element for receiving the radiation, whereby the measurement device is operably connected to a plurality of sensor-specific detector elements and generating a repeating drive pulse sequence containing drive pulses for the emitter elements of the plurality of sensors. The method further includes supplying the drive pulses of the drive pulse sequence to corresponding emitter elements, employing a parallel connection of the plurality of sensor-specific detector elements to produce a sequence of reception pulses at a terminal pair common to the sensor-specific detector elements, and receiving the electric reception signal at the measurement device.

All sensors of the device are not necessarily measurement sensors for making the actual pulse oximetry measurements. In one embodiment of the invention, the plurality of sensors includes at least one measurement sensor for making the actual measurement and at least one motion sensor for detecting physical motion of the subject. However, regardless of whether a sensor is a measurement sensor or a motion sensor, it comprises at least one emitter element and a sensor-specific detector.

Another aspect of the invention is that of providing a measurement arrangement for a measurement device configured to determine the attenuation of light in at least one subject. The measurement arrangement includes a plurality of sensors, each sensor comprising at least one emitter element for emitting radiation and a sensor-specific detector element for receiving the radiation, wherein the sensor-specific detector elements are connected in parallel for producing a sequence of reception pulses at a terminal pair common to the sensor-specific detector elements and a drive pulse generator unit configured to generate a repeating drive pulse sequence containing drive pulses for the emitter elements of the plurality of sensors. The measurement arrangement further includes a switching unit operably connected to the drive pulse generator unit and to the plurality of sensors, thereby to connect the drive pulses of the drive pulse sequence to corresponding emitter elements and a connection unit configured to connect the terminal pair operably to the measurement device, thereby to receive the sequence of reception pulses at the measurement device.

Since the additional hardware needed due to the multiple sensors may be minimized, the invention provides a cost-effective solution for devices intended for performing continuous non-invasive measurements through a plurality of optical sensors. This also translates to minimal area/space requirements allowing the implementation of compact size monitors.

A still further aspect of the invention is that of providing a computer program product by means of which an existing measurement device may be upgraded to carry out simultaneous measurements from a plurality of sensors. The computer product comprises a first program code portion configured to control the measurement device to generate a repeating drive pulse sequence containing drive pulses for the emitter elements of a plurality of sensors, a second program code portion configured to connect the drive pulses to respective emitter elements in a predetermined order, and a third program code portion configured to associate an electric reception signal with corresponding emitter elements of the plurality of sensors, one emitter element at a time according to the predetermined order.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 11 in the appended drawings, wherein.

DETAILED DESCRIPTION OF THE INVENTION

A monitoring or measurement device of the invention comprises a computerized measuring unit and a plurality of sensors. The sensors may be attached to multiple tissue sites and/or two or more of the sensors may be integrated into a single probe. Each sensor includes at least one light source, i.e. emitter element, for sending an optical signal and a photo detector for receiving the signal transmitted by the said at least one light source. The number of emitter elements in a sensor depends on the application used. Plethysmographic data, for example, may be measured with only one emitter element (one wavelength), but a pulse oximeter typically has two or more emitter elements in each sensor.

Figure 1:
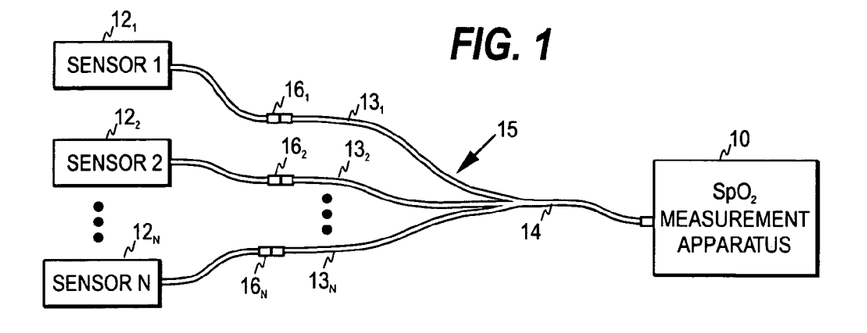
FIG. 1 illustrates a general measurement arrangement according to one embodiment of the invention.

FIG. 1 illustrates one embodiment of the general measurement arrangement of the invention. A single measurement or monitoring device 10, which is in this example a pulse oximeter, is provided with N sensors $12_1$ to $12_N$ attachable to multiple tissue sites. In the embodiment of FIG. 1, the actual measurement is performed through each sensor, i.e. each sensor is a measurement sensor.

As noted above, each sensor comprises at least one emitter element for emitting radiation at a minimum of one wavelength and a detector for receiving the radiation and for producing an electric signal in response to the radiation. The detectors may be standard multiwavelength detectors. A single measurement cable 15, comprising N branches, connects the detector of each sensor to the monitoring device. The measurement cable resembles a Y-shaped cable, but instead of the two oblique branches of a Y it comprises N branches $13_i$ (where $N \geq 2$ and $i=1, 2, \ldots, N$). A common cable segment 14 connects each branch to the monitoring device. Each sensor may be provided with a connector $16_i$ ($i=1 \ldots N$) for connecting the sensor to a mating connector mounted to the end of a respective branch of the measurement cable. In one embodiment of the invention, the mating connectors may be different from each other to allow the use of different sensors or sensors of different manufacturers.

Figure 2:
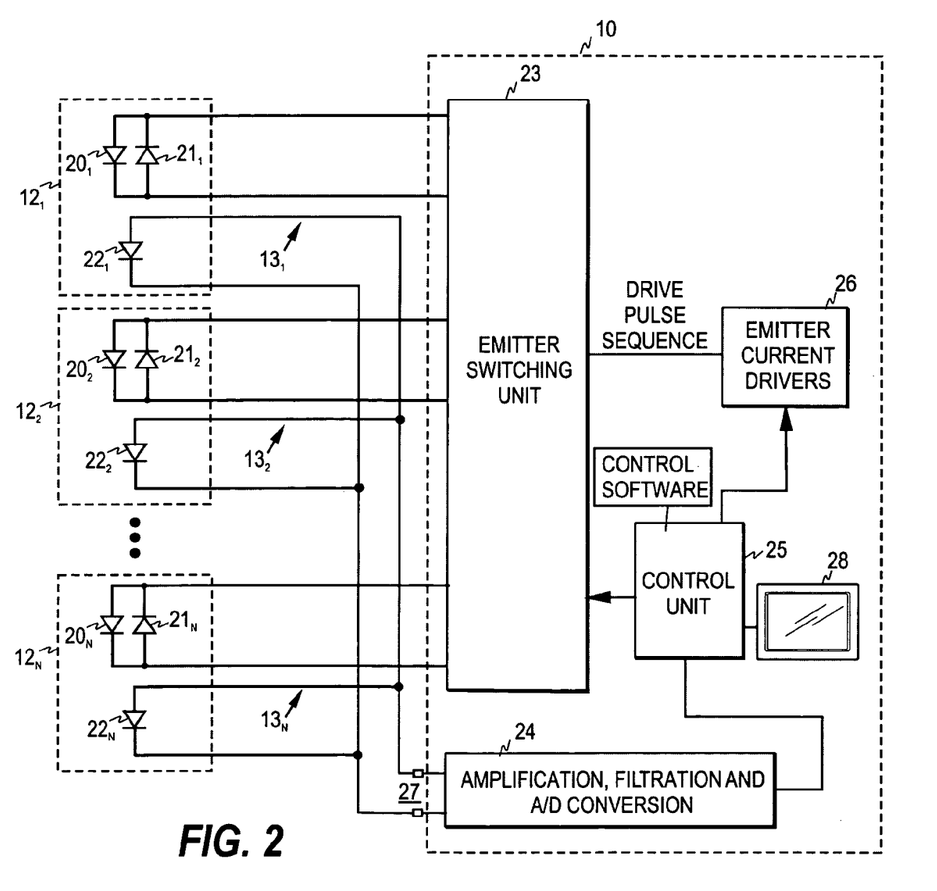
FIG. 2 illustrates one embodiment of the apparatus of the invention.

FIG. 2 illustrates one embodiment of the emitter and detector circuitries of the invention. In this example, each sensor $12_i$ comprises two LEDs $20_i$ and $21_i$ ($i=1, \ldots, N$) connected in parallel and back-to-back, i.e. in each sensor the anode of the first LED and the cathode of the second LED are connected together and form a first common pole, while the cathode of the first LED and the anode of the second LED are connected together to form a second common pole. Each sensor further comprises a sensor-specific photodetector $22_i$, which receives the light transmitted by the LEDs of the sensor and propagated through or reflected from the tissue and converts the optical signal into an electric signal. The sensor-specific detectors are connected in parallel, and the said electric signal is supplied to the monitoring device through a single anode/cathode wire pair, i.e. through the common cable segment 14 of FIG. 1. The detectors are thus connected to the monitoring device through a single terminal pair 27, i.e. similarly as the sensor is connected to the monitoring device in single-sensor monitoring device. Therefore, the reception branch 24 of the monitoring device may be implemented similarly as in a single-sensor monitoring device. The reception branch typically comprises an input amplifier, a bandpass filter, and an A/D converter. The digitized signal output from the A/D converter is supplied to a control unit 25, which processes the signal data and displays the analysis results on the screen of a display unit 28. The control unit is provided with control software that controls the activation of the LEDs in the sensors. Therefore, the control unit also knows from which one of the detectors the signal data originates in each time window.

The control unit controls an emitter current source 26 to generate a drive pulse sequence, which contains drive pulses for each emitter element in pre-allocated time windows. The drive pulse sequence is supplied to an emitter switching unit 23. The control unit controls the switches of the switching unit so that each drive pulse of the drive pulse sequence is supplied to the corresponding emitter element.

Figure 3:
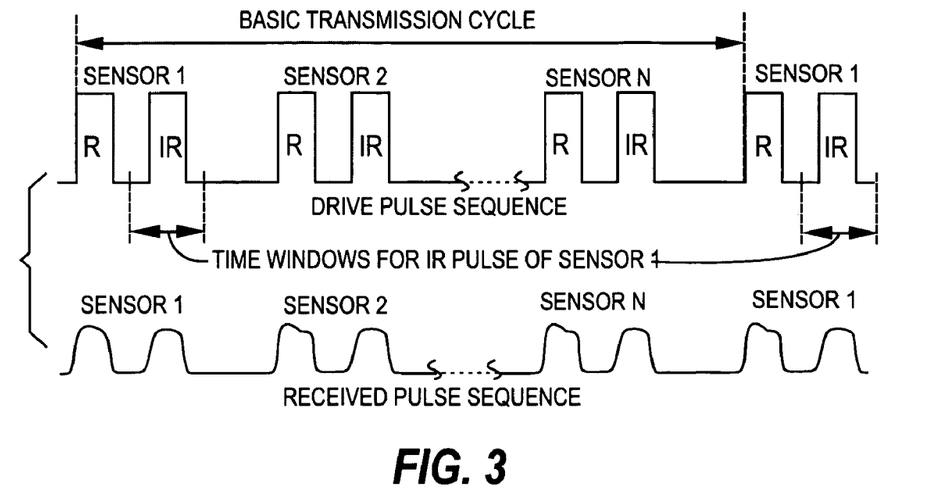
FIG. 3 illustrates one embodiment of the basic emitter and detector cycles of the apparatus of the invention.

FIG. 3 illustrates one embodiment of the repeating drive pulse sequence generated by the emitter current source and the corresponding detector signal received by the monitoring device. As noted above, each drive pulse has a pre-allocated time window within the drive pulse sequence. In other words, since the reception of the pulses is performed through a single wire pair, the drive pulses are time-multiplexed into the sequence and they do not overlap. Generally, the order of the drive pulses (i.e. the pulse pattern) may be arbitrary within the drive pulse sequence, but it is preferable that the two drive pulses of an individual sensor are after each other so that the time difference between the red and infrared pulses is minimized for each sensor. In the embodiment of FIG. 3, the sensors appear in order, i.e. each transmission cycle starts with the two drive pulses of the first sensor and ends after the two drive pulses of the $N^{th}$ sensor. Any known sequential control technique may, however, be used to drive the red and infrared emitter elements. For example, the pulse pattern may change as a function of time.

Figure 4:
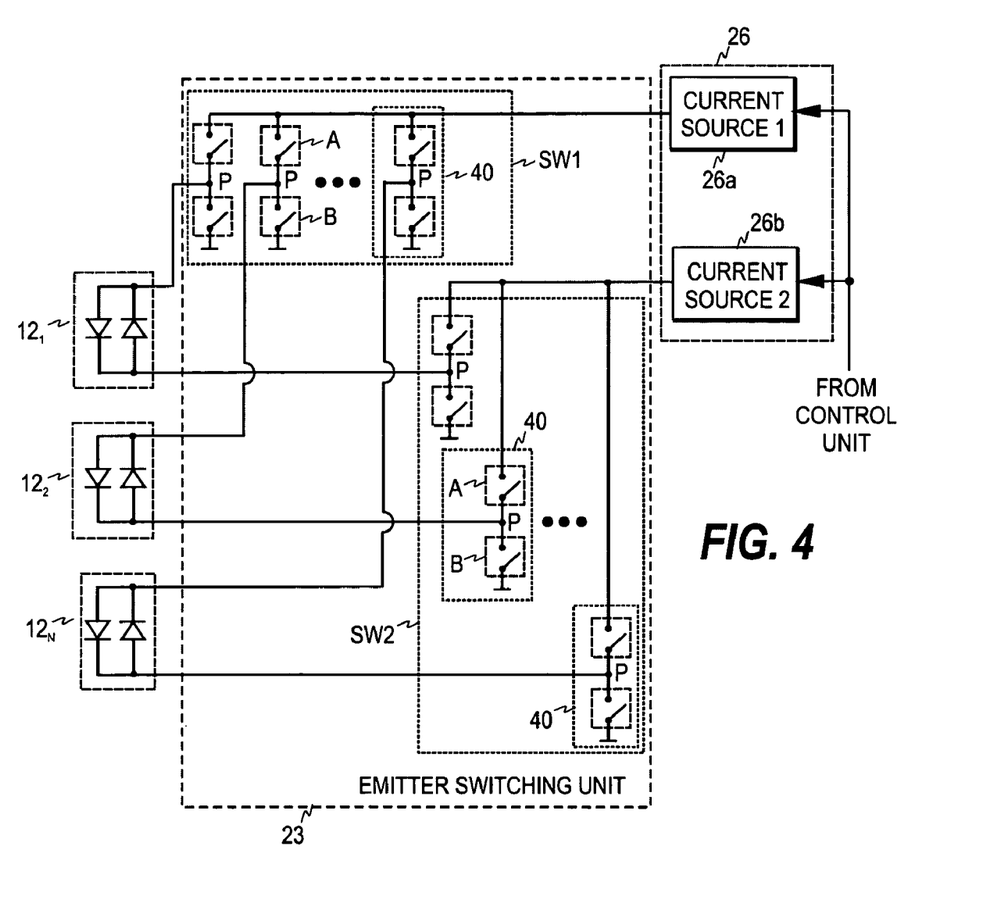
FIG. 4 illustrates one embodiment of the emitter switching unit of the apparatus of FIG. 2.

FIG. 4 illustrates one embodiment of the emitter current source 26 and the emitter switching unit 23. For reasons of clarity, the detectors have been omitted in the figure. The emitter current source comprises two current sources 26a and 26b, which output the pulse sequence of FIG. 3. In this embodiment, one of the current sources generates the pulses of all red emitter elements in the sensors, while the other current source generates the pulses of all infrared emitter elements in the sensors. Therefore, the first current source 26a is connected to the anodes of the emitter elements of the first type (red or infrared), while the second current source 26b is connected to the anodes of the emitter elements of the second type (infrared or red). The connection is formed through the emitter switching unit, which comprises 2N switching units 40, each of which comprises a first switching element A and a second switching element B connected in series.

The switching units may be divided into two groups: a first group SW1 comprising N units and a second group SW2 also comprising N units. The switching units of the first group switch the drive pulses output from the first current source to the emitter elements of the first type, while the switching units of the second group switch the drive pulses output from the second current source to the emitter elements of the second type. In each group, the first terminal of all switching elements A is connected to the output of the respective current source. The second terminal of all switching elements A is in turn connected to the anode of the emitter element driven by the respective current source. In each switching unit, the said second terminal is further connected to the first terminal of the second switching element B and the second terminal of the second switching element is connected to ground. The second terminal of the first switching elements and the first terminal of the second switching elements thus form a common pole P, which is connected to the anode of the emitter element driven by the respective current source and which may also be connected to ground through the respective second switching element. The first switching elements operate as drive switches which connect each current pulse to the correct emitter element, while the second switching elements operate as current sink switches.

Figure 5:
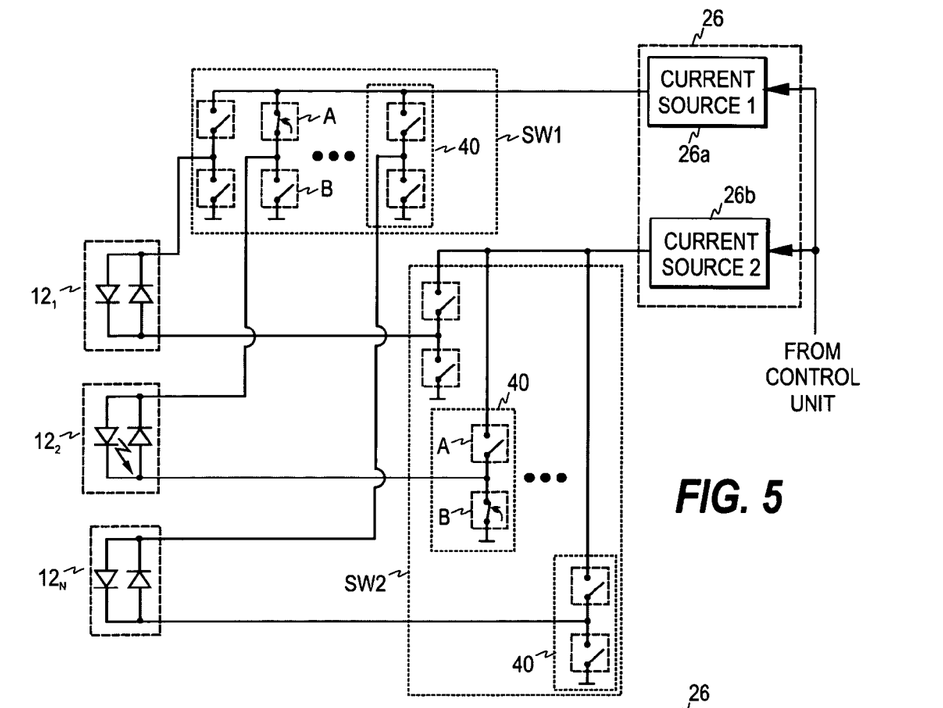
FIG. 5 and FIG. 6 illustrate the control of the emitter switching unit of FIG. 4 at two distinct time windows.
Figure 6:
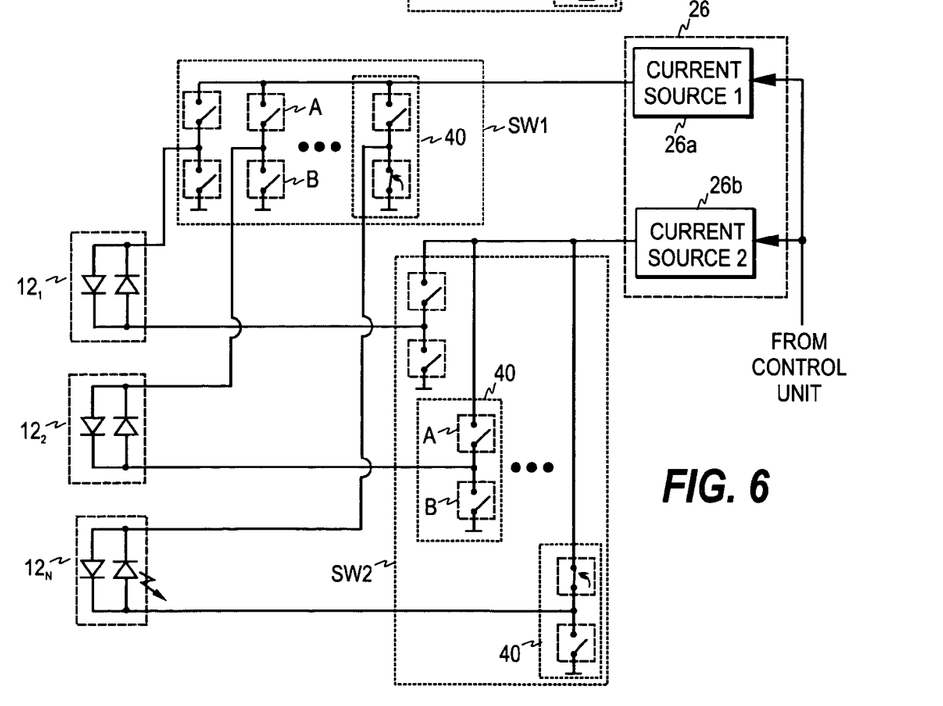

The control unit controls the switching elements so that when the drive pulse of the $i^{th}$ emitter element of the first type is output, switching element A in the $i^{th}$ switching unit of the first group and switching element B in the $i^{th}$ switching unit of the second group are closed (on). The other switching elements remain open (off). Correspondingly, when the drive pulse of the $i^{th}$ emitter element of the second type is output, switching element A in the $i^{th}$ switching unit of the second group and switching element B in the $i^{th}$ switching unit of the first group are closed (on). FIGS. 5 and 6 illustrate the control of the switching elements by showing the switches when the drive pulses of the second emitter element of the first type is output (FIG. 5) and when the drive pulses of the $N^{th}$ emitter element of the second type is output (FIG. 6).

The two current sources and the emitter switching unit enable current to be supplied through the sensors in both directions. In each time window corresponding to a drive pulse the control unit thus closes two of the switching elements, the said two elements being selected in accordance with the emitter element to which the time window is allocated.

Figure 7:
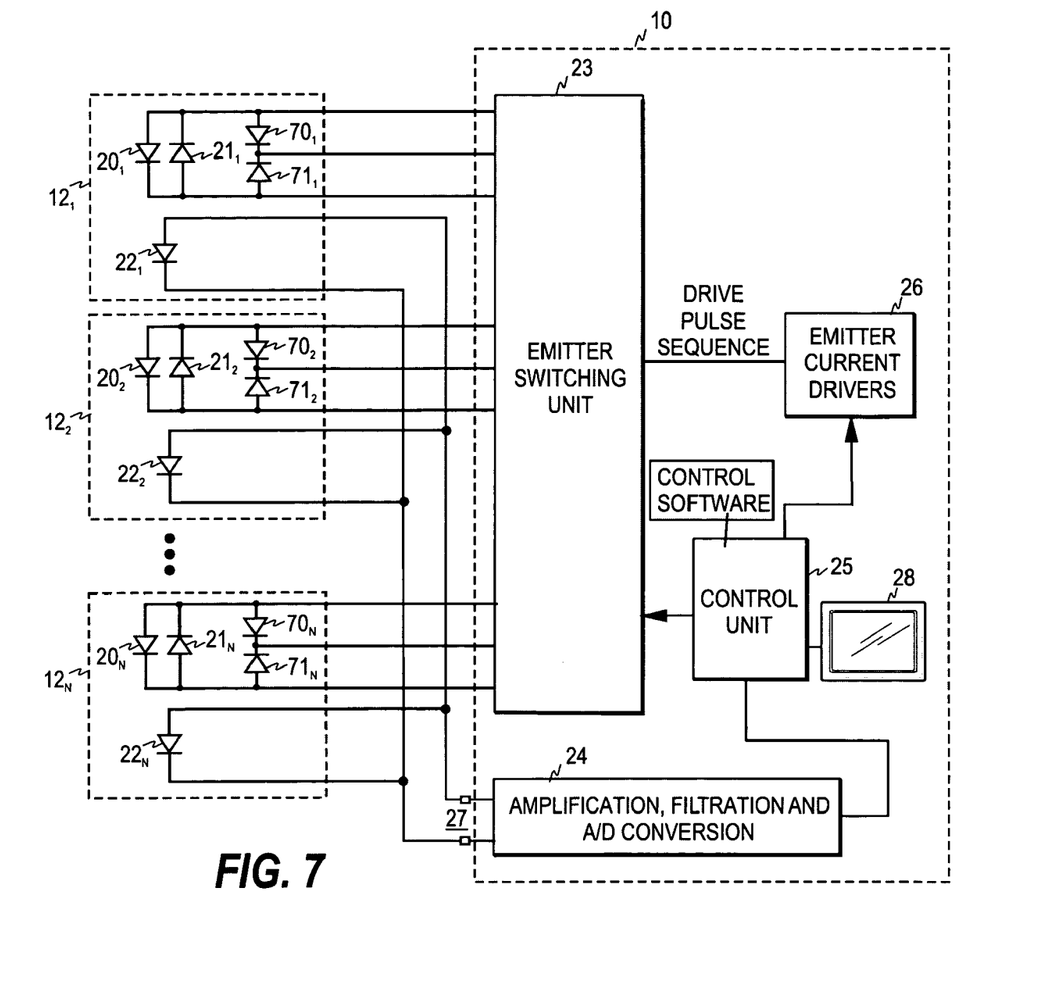
FIG. 7 illustrates an embodiment of the apparatus comprising sensors emitting at four different wavelengths.

As noted above, each sensor may be provided with one or more emitter elements. FIG. 7 illustrates an embodiment of the invention, in which each sensor comprises four emitter elements emitting, respectively, at four wavelengths. In comparison with the embodiment of FIG. 2, each sensor now further includes a third LED $70_i$ and a fourth LED $71_i$ ($i=1$, 2, ... N). In each sensor, the anode of the third LED $70_i$ is connected to the terminal formed by the anode of the first LED and the cathode of the second LED and the anode of the fourth LED $71_i$ is connected to the terminal formed by the cathode of the first LED and the anode of the second LED. The cathodes of the third and fourth LEDs are connected together. In comparison with the embodiment of FIG. 4, the embodiment of FIG. 7 does not require additional switching elements, since each third and fourth LED may still be driven through one of switching units in the first and second groups, respectively, and the common cathode of each LED pair may be connected to ground through one of the switching elements shown in FIG. 4, so that each LED may be illuminated in a dedicated time window of the drive pulse sequence.

Although the sensors are typically similar in regard to the wavelengths used, it is possible, depending on the application, that the sensors operate at different wavelengths with respect to each other.

Figure 8:
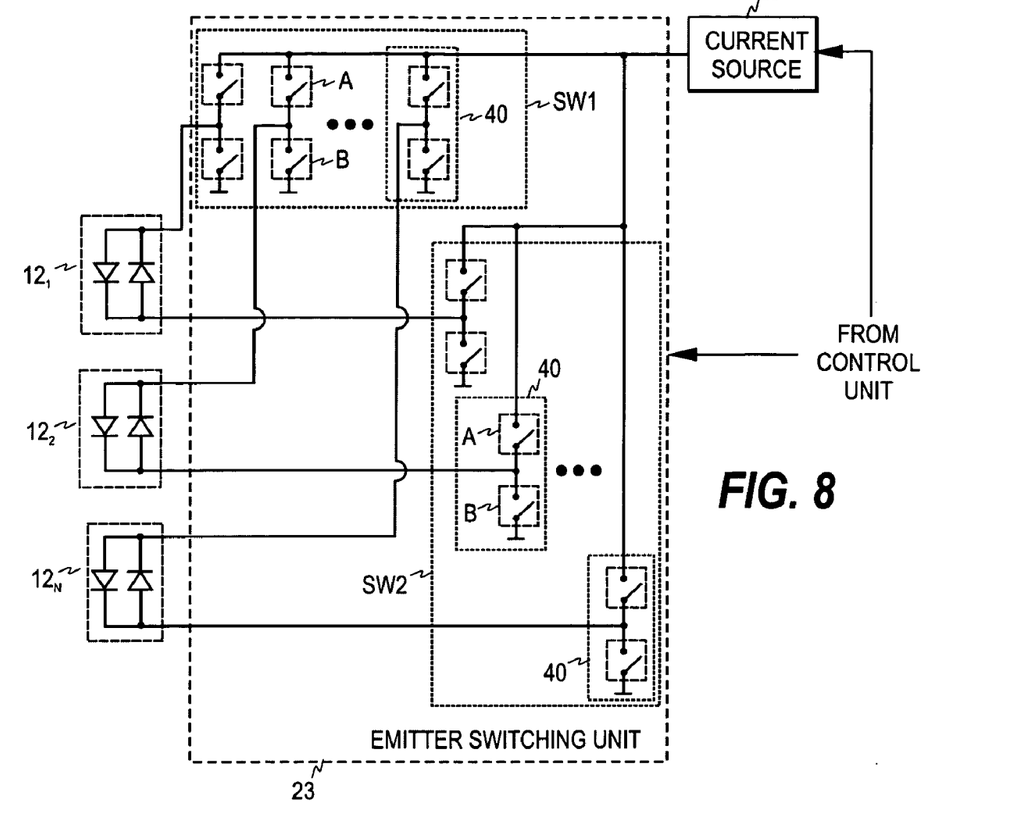
FIG. 8 illustrates one embodiment of the monitoring device of the invention, which comprises a common current source for all emitter elements.

The pulse power supplied to the red emitter elements is typically different from the pulse power supplied to the infrared emitter elements. Therefore, it is advantageous to use a dedicated current source for both emitter element types, as each current source may then use a preset pulse power. However, if the power of a current source may be controlled with sufficient accuracy on a pulse-by-pulse basis, the number of the current sources in the emitter current source may be reduced to one. An embodiment comprising a common current source for all emitter elements of the plurality of sensors is illustrated in FIG. 8. The embodiment shown in the figure corresponds otherwise to the embodiment of FIG. 4, but a single current source 29 connected to both switching unit groups SW1 and SW2 now drives all the emitter elements.

Since at most two current sources are needed for the plurality of sensors operating at one or more wavelengths, the above-described measurement arrangement enables a cost-effective implementation of a monitoring device with multiple sensors. This is due to the fact that the number of current sources (which are relatively expensive) and the number of connection wires may be kept low. Furthermore, no hardware multiplication is needed for the reception side of the monitoring device.

In a further embodiment of the invention, at least one of the sensors may be utilized for detecting physical motion of the subject, whereas the actual measurement, such as $SpO_2$ measurement, is performed through at least one other sensor, i.e. a measurement sensor.

Figure 9:
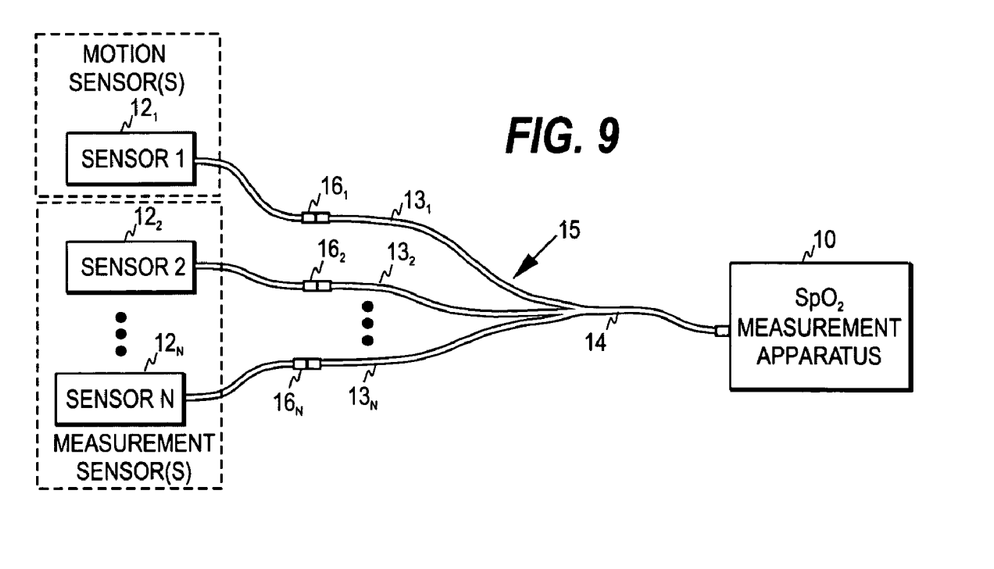
FIG. 9 illustrates a general measurement arrangement according to a further embodiment of the invention.

FIG. 9 illustrates one embodiment of a device comprising different types of sensors. As in the embodiment of FIG. 1, the measurement or monitoring device 10 is provided with N sensors $12_1$ to $12_N$. However, in this embodiment K sensors out of the N sensors are motion sensors, while (N-K) sensors are actual measurement sensors ($K=1, 2, \ldots, (N-1)$). It is assumed in FIG. 9 that K=1. Regardless of whether a sensor is a measurement sensor or a motion sensor, it includes at least one light source and a sensor-specific photo detector. As discussed above, the number of emitter elements in a measurement sensor depends on the application used. A motion sensor, however, typically includes only one emitter element. The detectors of all sensors may be standard multiwavelength detectors. Similarly as in the embodiment of FIG. 1, the measurement cable 15 connects the detector of each sensor to the measurement device. In one embodiment of the invention, the mating connectors $16_i$ used by the motion sensors may be different from those used by the measurement sensors, or the mating connectors of either type of sensors may be different from each other to allow the use of sensors of different manufacturers.

Figure 10:
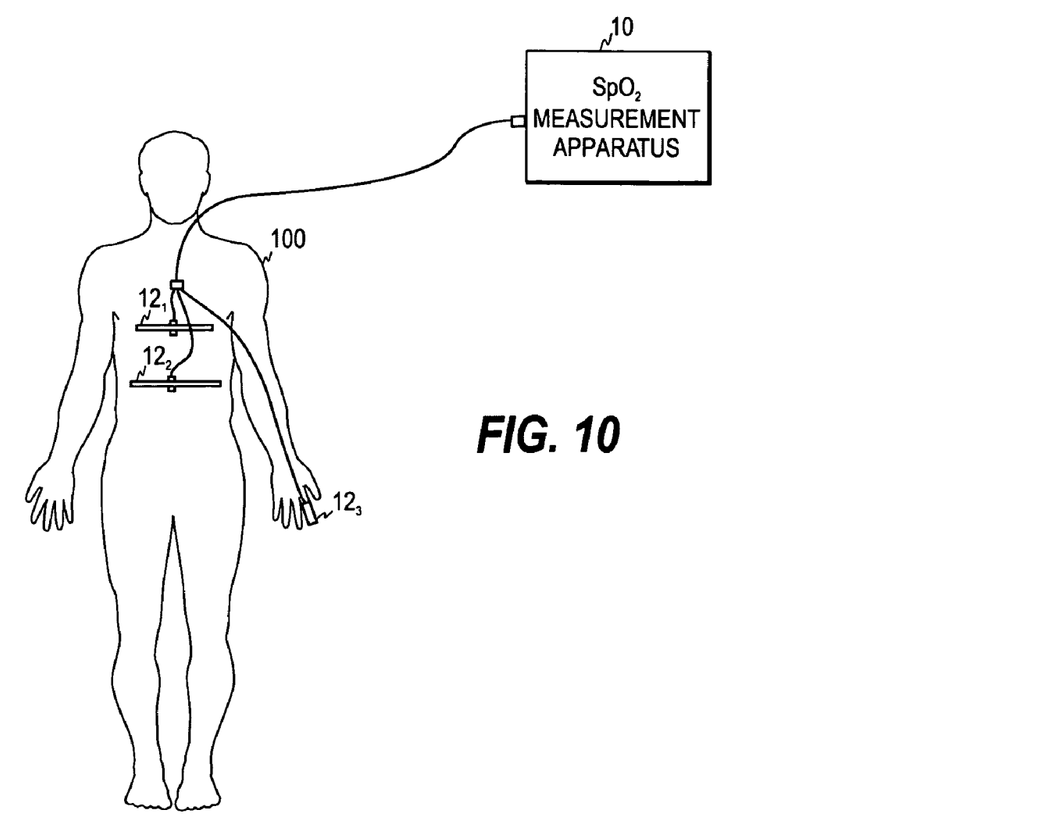
FIG. 10 illustrates one embodiment of the measuring arrangement of FIG. 9 for monitoring respiration during $SpO_2$ measurement.

In one embodiment of the invention, which is shown in FIG. 10, the measurement arrangement comprises one measurement sensor $12_3$ for $SpO_2$ measurement, for example, and two motion sensors $12_1$ and $12_2$ for detecting motion. In this embodiment, the motion sensors are configured to monitor the respiration of subject 100. For this purpose, the motion sensors may comprise cheap and easy to use sticker band or belt type strain sensors of which one is attached onto the chest and the other onto the midriff of the subject. The external pressure originating from the chest and midriff movements alternates the distance between the emitter and detector in the respective motion sensor, thereby modulating the intensity of the output signal of the respective sensor. By placing a motion sensor both on the chest and midriff areas, an indication may be obtained of the depth of the respiration.

The motion sensors $12_1$ and $12_2$ may comprise, for example, an optical strain-gauge transducer for sensing the respiration contractions, i.e. for converting the respiration motion into an electric signal. The measurement sensor $12_3$ may be in the form of a conventional finger probe, for example.

The embodiment of FIG. 10 is advantageous in all medical applications requiring $SpO_2$ and respiration measurements, and especially advantageous in medical applications requiring $SpO_2$ and respiration measurements only, since no dedicated equipment is needed for obtaining the respiratory signal.

Instead of or in addition to respiration, the motion sensor(s) may also be used for detecting motion artefacts.

Figure 11:
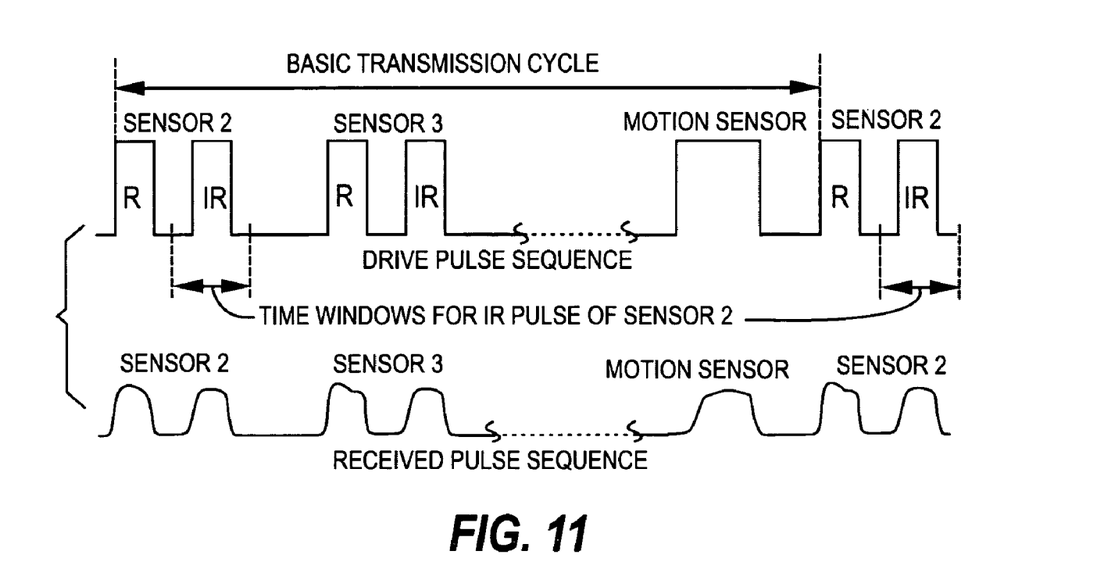
FIG. 11 illustrates a further embodiment of the basic emitter and detector cycles of the apparatus of the invention.

FIG. 11 illustrates one embodiment of the repeating drive pulse sequence generated by the emitter current source 26 and the corresponding detector signal received by the measurement device, when the device is provided with one motion sensor and a plurality of measurement sensors. In the embodiment of FIG. 11, the sensors appear in order and the drive pulse of the only motion sensor is the last one in the sequence. Each transmission cycle thus starts with the two drive pulses of the first measurement sensor (sensor 2) and ends after the drive pulse of the motion sensor. The pulse length of the motion sensor may be different from that of the measurement sensors. Otherwise, the drive pulse sequence may be modified as discussed in connection with FIG. 3.

In the embodiments comprising at least one motion sensor, the reception pulses obtained from the motion sensor(s) are discriminated from the reception pulses obtained from the at least one measurement sensor and the pulses obtained from the motion sensor(s) are employed to detect physical motion of the subject during the measurement performed through the at least one measurement sensor. The discrimination of the pulses may be performed in the control unit, which processes the signal data.

As the present invention may utilize a conventional measurement branch 24 of a single-sensor monitoring device, a conventional monitoring device may be upgraded by providing it with a transmission side capable of connecting each drive pulse to a corresponding emitter element and with a plug-in control software module that enables the device to operate in the time-multiplexed manner described above. The control software module may be delivered, for example, on a data carrier, such as a CD or a memory card, or via a telecommunications network. The software module may be divided into three logical portions according its operation: the first program code portion is configured to control the monitoring device to generate a repeating drive pulse sequence containing drive pulses for all emitter elements of the plurality of sensors, the second program code portion is configured to connect the drive pulses to respective emitter elements in a predetermined order, and the third program code portion is configured to associate an electric reception signal with corresponding emitter elements, one emitter element at a time according to the predetermined order.

Although the invention was described above with reference to the examples shown in the appended drawings, it is obvious that the invention is not limited to these, but may be modified by those skilled in the art without departing from the scope and spirit of the invention. For example, the analysis performed in the control unit on the basis of the measured attenuation may vary according to the application in question. As indicated above, the attenuation may be indicative of the amount of at least one light absorbing substance in the subject. In addition to pulse oximetry, the device may be used, for example, to monitor blood circulation at various tissue sites in connection with blood surgery or to measure the delay associated with the pulsating blood component at various tissue sites. It is also possible that the measurement sensors of the device include sensors for more than one application.

The invention claimed is:

1. A measurement method for a measurement device configured to determine the attenuation of light in at least one subject, the method comprising:
   connecting the measurement device operably to a plurality of sensors, each sensor comprising at least one emitter element for emitting radiation and a sensor-specific detector element for receiving the radiation, whereby the measurement device is operably connected to a plurality of sensor-specific detector elements;
   generating a repeating drive pulse sequence containing drive pulses for the emitter elements of the plurality of sensors;
   supplying the drive pulses of the drive pulse sequence to corresponding emitter elements;
   employing a parallel connection of the plurality of sensor-specific detector elements to produce a sequence of reception pulses at a terminal pair common to the sensor-specific detector elements; and
   receiving the sequence of reception pulses at the measurement device.

2. A method according to claim 1, wherein each sensor comprises a first emitter element for emitting radiation at a first wavelength and a second emitter element for emitting radiation at a second wavelength, whereby the plurality of sensors comprise a plurality of first emitter elements and a plurality of second emitter elements.

3. A method according to claim 2, wherein the generating includes producing the drive pulse sequence by means of a first current source generating drive pulses for the plurality of first emitter elements and a second current source generating drive pulses for the plurality of second emitter elements.

4. A method according to claim 3, wherein the supplying includes controlling a first switching element for connecting a drive pulse to the anode of a selected emitter element and a second switching element for connecting the cathode of the selected emitter element to ground, wherein the selected emitter element is one of the emitter elements of the plurality of sensors.

5. A method according to claim 1, wherein the receiving includes connecting the sensor-specific detector elements to the measurement device through a patient cable comprising parallel branches for the plurality of sensors.

6. A method according to claim 1, wherein the generating includes controlling the power of the drive pulses on a pulse-by-pulse basis.

7. A method according to claim 1, wherein the connecting includes connecting the measurement device operably to the plurality of sensors, wherein the plurality of sensors comprises at least one motion sensor and at least one measurement sensor.

8. A method according to claim 7, further comprising
   discriminating the reception pulses obtained from the at least one motion sensor from the reception pulses obtained from the at least one measurement sensor; and
   utilizing the reception pulses obtained from the at least one motion sensor to detect a physical motion of the at least one subject during a measurement based on the reception pulses obtained from the at least one measurement sensor.

9. A method according to claim 8, wherein the utilizing includes utilizing the reception pulses obtained from the at least one motion sensor to detect the physical motion, wherein the physical motion is caused by respiration of the at least one subject.

10. A method according to claim 8, wherein the utilizing includes utilizing the reception pulses obtained from the at least one motion sensor to detect the physical motion, wherein the physical motion is caused by unwanted movement of the at least one subject.

11. A measurement arrangement for a measurement device configured to determine the attenuation of light in at least one subject, the measurement arrangement comprising:
   a plurality of sensors, each sensor comprising at least one emitter element for emitting radiation and a sensor-specific detector element for receiving the radiation, wherein the sensor-specific detector elements are connected in parallel for producing a sequence of reception pulses at a terminal pair common to the sensor-specific detector elements;
   drive pulse generator unit configured to generate a repeating drive pulse sequence containing drive pulses for the emitter elements of the plurality of sensors;
   a switching unit operably connected to the drive pulse generator unit and to the plurality of sensors, thereby to connect the drive pulses of the drive pulse sequence to corresponding emitter elements; and
   a connector unit configured to connect the terminal pair operably to the measurement device, thereby to receive the sequence of reception pulses at the measurement device.

12. A measurement arrangement according to claim 11, wherein each sensor comprises a first emitter element for emitting radiation at a first wavelength and a second emitter element for emitting radiation at a second wavelength, whereby the plurality of sensors comprise a plurality of first emitter elements and a plurality of second emitter elements.

13. A measurement arrangement according to claim 12, wherein the drive pulse generator unit comprises a first current source configured to generate drive pulses for the first emitter elements and a second current source configured to generate drive pulses for the second emitter elements.

14. A measurement arrangement according to claim 11, wherein the switching unit comprises a first group of switching units for the first emitter elements and a second group of switching units for the second emitter elements, each switching unit comprising a first switching element and a second switching element connected in series.

15. A measurement arrangement according to claim 14, wherein
- the first current source is operably connected to each first switching element of the first group for connecting each drive pulse to the anode of the corresponding emitter element and the second current source is operably connected to each first switching element of the second group for connecting each drive pulse to the anode of the corresponding emitter element, and
- each second switching element is connected to ground for connecting the cathode of the corresponding emitter element to ground.

16. A measurement arrangement according to claim 11, wherein the connector unit comprises a patient cable comprising parallel branches for the plurality of sensors.

17. A measurement arrangement according to claim 11, wherein the drive pulse generator unit comprises a single current source for generating the drive pulse sequence.

18. A measurement arrangement according to claim 11, wherein the plurality of sensors comprises at least one motion sensor and at least one measurement sensor.

19. A measurement arrangement according to claim 18, further comprising a discrimination module configured to discriminate the reception pulses obtained from the at least one motion sensor from the reception pulses obtained from the at least one measurement sensor.

20. A measurement arrangement according to claim 18, wherein at least one of the at least one motion sensor is configured to measure respiration of the at least one subject.

21. A measurement arrangement according to claim 18, wherein at least one of the at least one motion sensor is configured to measure unwanted movement of the at least one subject.

22. A measurement arrangement for a measurement device configured to determine the attenuation of light in at least one subject, the measurement arrangement comprising:
- a plurality of sensors, each sensor comprising at least one emitter element for emitting radiation and a sensor-specific detector element for receiving the radiation, wherein the sensor-specific detector elements are connected in parallel for producing a sequence of reception pulses at a terminal pair common to the sensor-specific detector elements;
- drive pulse generator means for generating a repeating drive pulse sequence containing drive pulses for the emitter elements of the plurality of sensors;
- switching means operably connected to the drive pulse generator means and to the plurality of sensors for connecting the drive pulses of the drive pulse sequence to corresponding emitter elements; and
- connector means for connecting (1) the switching means to the emitter elements and (2) the terminal pair to the measurement device for receiving the sequence of reception pulses at the measurement device.

* * * * *